United States Patent [19]

Givner et al.

[11] 4,033,723
[45] July 5, 1977

[54] PREGNANCY TEST DEVICE

[75] Inventors: Morris Lincoln Givner, Pierefonds; Guenther Schilling, Westmount, both of Canada

[73] Assignee: American Home Products Corporation, New York, N.Y.

[22] Filed: Dec. 31, 1975

[21] Appl. No.: 645,860

[30] Foreign Application Priority Data

Dec. 17, 1975 Canada .............. 242214

[52] U.S. Cl. .................. 23/253 R; 23/259; 210/22 R; 210/23 F; 210/284; 210/317; 210/321 A; 424/12

[51] Int. Cl.² ............... B01D 31/00; G01N 21/04; G01N 33/16

[58] Field of Search ............ 424/12; 23/230 B, 259, 23/253 R, 233 R; 210/23 F, 22, 321 A, 284, 317

[56] References Cited

UNITED STATES PATENTS

| 3,689,633 | 9/1972 | Sanae .................... 424/12 |
| 3,783,127 | 1/1974 | Cook .................. 210/321 A |
| 3,817,379 | 6/1974 | Zipilivan ................ 210/94 |
| 3,873,682 | 3/1975 | Ogawa .................... 424/12 |
| 3,873,683 | 3/1975 | Fishbein ................. 424/12 |

*Primary Examiner*—Sidney Marantz

[57] ABSTRACT

A simple, sensitive method and device for detecting pregnancy. The test involves concentration by ultrafiltration of a sample of urine or serum from a subject; followed by determining the presence of human chorionic gonadotropin or of its β-subunit in the concentrated sample.

10 Claims, 19 Drawing Figures

U.S. Patent    July 5, 1977    Sheet 1 of 5    4,033,723
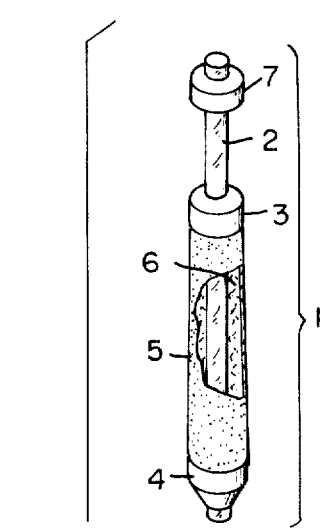
FIG. 1
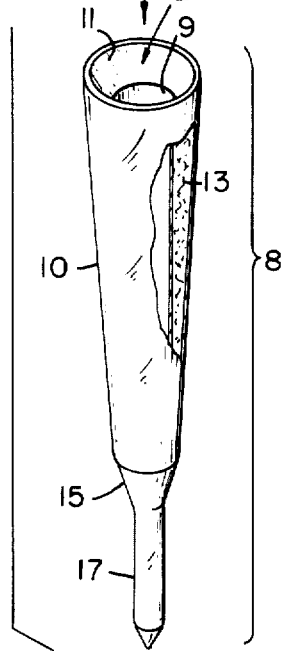
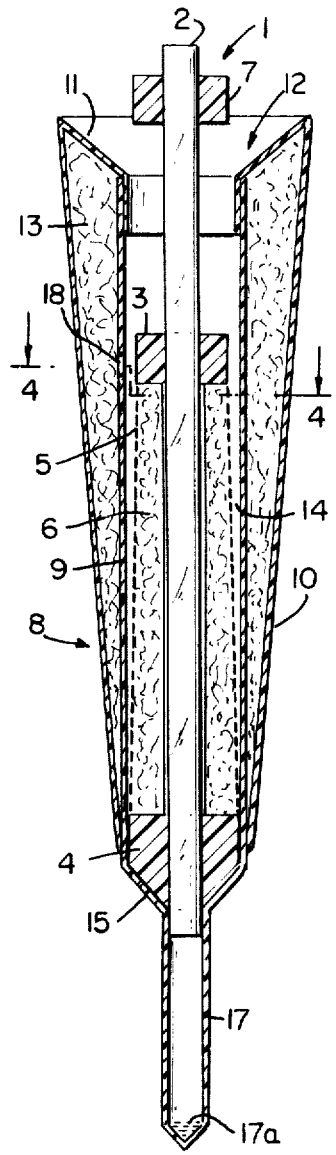
FIG. 2
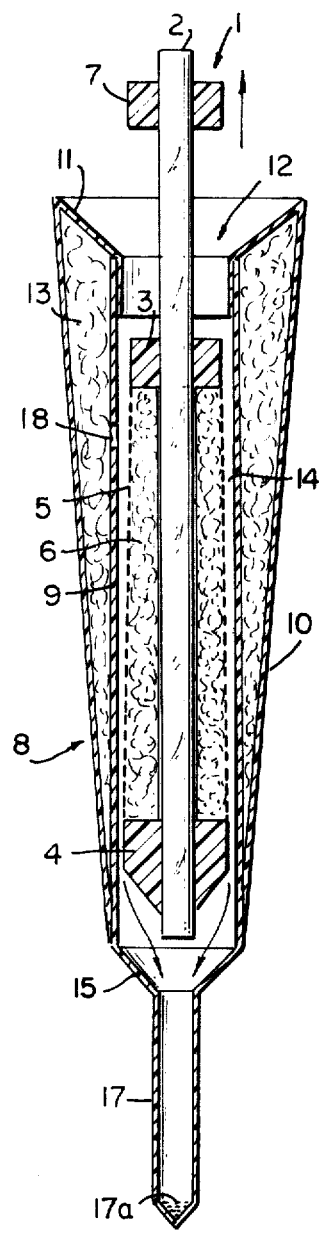
FIG. 3
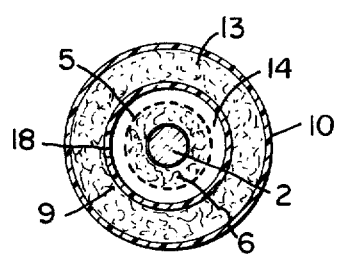
FIG. 4

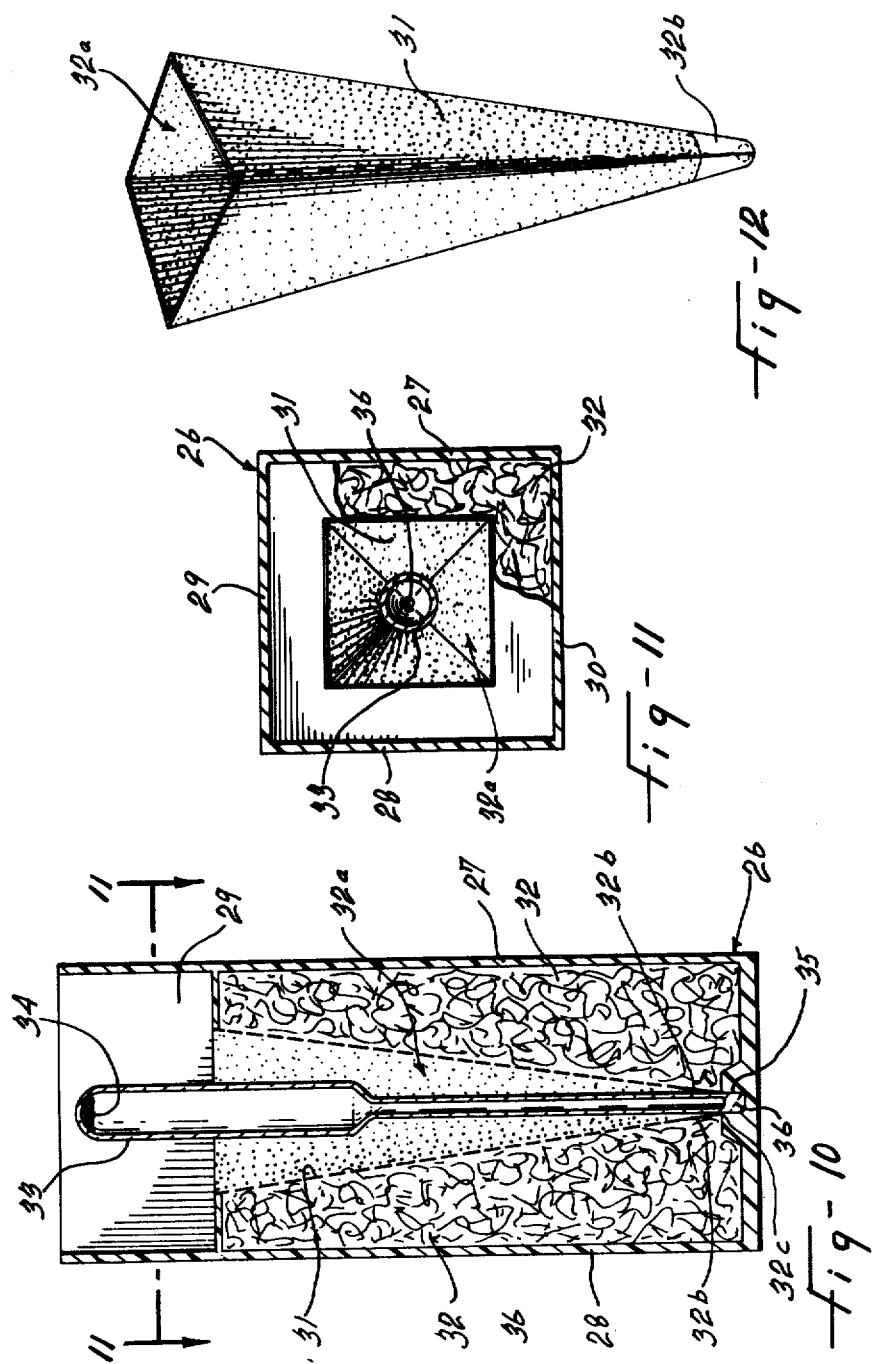

PREGNANCY TEST DEVICE

BACKGROUND OF THE INVENTION a. Field of the Invention

This invention relates to a method and device for detecting pregnancy. More specifically, this invention concerns a simple and sensitive method and device for the detection of pregnancy in women; the method and device being especially useful for the detection of pregnancy in its very early stages.

b. Prior Art

A simple, sensitive test for the early diagnosis of human pregnancy would be an important contribution to medicine and society. For instance, it would be advantageous in cases of unwanted pregnancies or in cases of habitual aborters who would benefit from early therapy. It would also be advantageous for the physician to have knowledge of an early pregnancy before prescribing a drug that may be teratogenic, or in those instances where a woman has unwittingly been exposed to a possibly teratogenic drug. Also, not to be overlooked, is the all important psychological factor for the woman to know for certain whether she is pregnant or not.

The most widely used pregnancy tests employed today are those based on the detection of human chorionic gonadotropin (HCG) in urine samples by immunological methods. These tests rely on the fact that HCG is the gonadotropin of pregnancy, being secreted by the chorionic tissue of the placenta in increasing amounts soon after the implantation therein of a fertilized ovum ]The peak secretion of HCG of more than 50,000 i.u. per a 24 hour collection of urine occurs between 56 and 84 days after the mentrual priod, E. H. Venning in "Text Book of Gynecologic Endocrinology," J. J. Gold, Ed., Harper and Row, New York, 1968, pp. 95 – 97. These tests are generally reliable for detecting pregnancy after about the 12th day following a missed menstrual period (i.e., about the 40th day of amenorrhea) giving about a 2 to 6% error when correctly performed, B. M. Hibbard, Brit. Med. J., 1, 593 (1971) and C. A. Horwitz, et al., Obstet. Gynecol., 43, 693 (1974). However, the tests cannot be relied upon prior to that time since they only can detect minimum concentrations of HCG of about 1000 – 3000 m. i.u./ml. of urine. The main reason for not increasing the sensitivity of these tests is to avoid false positives resulting from substances which cross react with the HCG-antiserum, B. M. Hobson, J. Reprod. Fertil., 12, 33 (1966).

Recently, more sensitive tests have been developed. These newer tests are based on sensitive but sometimes non-specific radioimmunoassay (RIA) techniques. The non-specificity of these tests arises from the fact that they also give positive results with other gonadotropins such as human pituitary luteinizing hormone (LH), i.e., the antisera to HCG may cross react with LH. Using the non-specific RIA techniques, LH-HCG has been shown to rise sharply beginning 10 to 14 days after the mid-cycle LH peak in the first month of pregnancy. For example, see R. B. Jaffe, et al., J. Clin. Endocrinol. Metabol., 29, 1281 (1969); A. F. Parlow, et al., J. Clin. Endocrinol. Metabol., 31, 213 (1970); D. P. Goldstein, et al., Fertil, Steril., 23 817 (1972), L. Wide, Lancet, 2, 863 (1969); and D. R. Mishell, Jr., et al., Am. J. Obstet. Gynecol., 117, 631 (1973).

A RIA also has been developed which is specific for the beta subunit of HCG. This latter test has been used to measure serum or plasma HCG by RIA in the presence of circulating LH during the same early period of pregnancy. See, for example, L. Wide, Lancet, 2, 863 (1969), T. S. Kosasa, et al., J. Clin. Endocrinol. Metabol., 36, 622 (1973); and T. S. Kosasa, et al., Obstet. Gynecol., 42, 868 (1973).

Although RIA techniques are sensitive, it will be appreciated that these methods are expensive and complex. They must be performed by highly trained personnel using isotopic material and very sophisticated equipment.

Another test is the radio-receptor assay for HCG recently developed by B. B. Saxera, et al., Science, 184, 793 (1974). Although less time-consuming than the RIA, this test also requires both special equipment and an operator with technical skills.

Another group of tests for pregnancy are the biological tests, including the well known "rabbit test." For a review on these and other tests see B. M. Hobson, cited above. It is a well known fact, however, that these biological tests are laborious and time-consuming. Furthermore, they require the maintenance of colonies of animals, the animals being subject to seasonal variations in sensitivity.

Still other pregnancy tests have been reported. These other tests depend on estimations of serum steroid levels or on the observation of withdrawal bleeding after progestogen alone or progestrogen-estrogen therapy. These tests are considered to be less reliable than other tests discussed above.

In accordance with the need for a simple and sensitive test for the detection of pregnancy, the present invention provides a method and a device for such a test based on the concept of ultrafiltration of body fluid (e.g., urine, serum or plasma) followed by immunological determination of HCG. Ultrafiltration has been used to concentrate initially high titres of "trophoblastic tumor HCG," in urine, M. L. Taymor, et al., J. Endocrinol., 36, 417 (1966) and S. Lok, Asian J. Med., 9, 319 (1973). Such tumors produce high levels of "trophoblastic HCG", much higher than those encountered in pregnancy. Taymor, et al. concentrated the high "trophoblastic titre HCG" urine in a step directed to the purification of this gonadotropin. Incidentally, these tumors occur only rarely. It should be noted that trophoblastic tumors will give a positive test in the present invention. Accordingly, in the case where the present method gives a positive test which is later shown to be false in regards to pregnancy, such HCG producing tumors should be suspected.

The present invention provides a convenient method and device for detecting pregnancy, especially in the early stages, the method being reliable and easily performed. Furthermore, the invention provides a method giving a substantial reduction in false positives and false negatives compared to prior art non-radioactive methods.

SUMMARY OF THE INVENTION

According to one aspect of the present invention a simple and sensitive pregnancy test method for detecting HCG or its β-subunit in the urine or serum of a subject, particularly in the urine or serum of female humans, is effected by a process comprising:

a. concentrating the urine or serum sample by ultrafiltration through a membrane having a molecular cut-off rendering the membrane impermerable to human chorionic gonadotrophin, and b. detecting the presence of human chorionic gonadotropin or its β-subunit in the concentrated sample by immunological or physical means, preferably by an agglutination or agglutination inhibition test.

A preferred embodiment of the above method includes the step of clarification of the urine sample by filtration or centrifugation prior to concentration.

According to another aspect of this invention, a device suitable for the detection of pregnancy, including early pregnancy, by means of ultrafiltration concentrated biological fluid selected from the group of urine and serum containing human chorionic gonadotropin and/or a subunit thereof is provided. The device includes a chamber, open at the top and closed at the bottom, having the upper portion of at least one wall formed of an ultrafiltration membrane permeable to urine or serum and capable of selective retention of human chorionic gonadotropin, all other walls being formed of a rigid impermeable material, and a layer of absorbent capable of sorbing urine or serum passing through the membrane, the absorbent being contiguous to the outside surface of the membrane and in effective contact with the membrane. The chamber further includes a lower portion, all walls of which are impermeable, for retaining a fixed volume of urine or serum concentrate containing human chorionic gonadotropin, outlet means in the lower portion of the chamber, means for opening the outlet means, and a reagent receptacle connected to the chamber through the outlet means, the reagent receptacle adapted to receive a reagent for the immunological determination of human chorionic gonadotropin or its β-subunit and means for viewing the reaction of the reagent therein with the said urine or serum concentrate containing human chorionic gonadotropin.

An embodiment of the device of this invention includes a filter disposed for filtering urine being introduced into the chamber.

DETAILS OF THE INVENTION

The term "molecular cut-off" as used herein refers to the capacity of an ultrafiltration membrane to retain 80 to 100% of those molecules having a molecular weight equal to or greater than the number associated with the term, while allowing those molecules of lesser molecular weight to pass through the membrane.

The term "false positive" as used herein contemplates the occurence of a positive test result when it can be demonstrated unequivocally by other methods that the test result should be negative.

The term "expected date of menses" as used herein refers to the 28th day after the first day of the last menses.

It will be appreciated by those skilled in the gonadotropin art that the immunological determination of the β-subunit of HCG is possible whether the β-subunit is separate or incorporated in the HCG molecule. For the purpose of this invention the detection of the β-subunit in either form is effective.

The first step of the pregnancy testing method of this invention involves concentrating by ultrafiltration a sample of urine or serum. In the case of the concentration of urine, a sample from the first morning urination preferably is used. The ultrafiltration is effected by means of an ultrafiltration membrane. A number of such ultrafiltration membranes are described by W. F. Blatt in "Methods in Enzymology" Vol. XXII, W. B. Jakoby, Ed., Academic Press, New York and London, 1971; V. E. Pollak, et al., J. Lab. Clin. Med., 71, 338 (1968); W. F. Blatt, et al., Nature, 216, 511 (1967); and W. F. Blatt, et al., Science 150, 224 (1965); as well as in U.S. Pat. No. 3,549,016, issued Dec. 22, 1970; and U.S. Pat. No. 3,615,024, issued Oct. 26, 1971.

Examples of suitable ultrafiltraton membranes includues those of the anisotropic, aromatic polymer type, for instance, Diaflo PM-10, Diaflo PM-20 (Amicon Corp) and Diaflo PM-30 (Amicon Corp), and Iopor AP and Iopor XP (Dorr-Oliver, Stamford, Conn.); the anisotropic, cellulosic type, for instance, HFA-100 and HFA-200 (Abcor Inc., Cambridge, Mass.) and PSED (Millipore Corp., Bedford, mass.); and gel cellophane such as manufactured by du Pont Chemicals, Wilmington, Del. or Union Carbide, N.Y.C.

Methods and apparatus for concentration by ultrafiltration of the aforementioned sample are described in the above references pertaining to ultrafiltration membranes. Particularly useful designs for ultrafiltration concentrators are described also by P. N. Rigopulos in U.S. Pat. No. 3,488,768, issued Jan. 6, 1970; by H. H. Loeffler in U.S. Pat. No. 3,565,256, issued Feb. 23, E. M. Zipilivan, et al., in U.S. Pat. No. 3,817,379, issued June 18, 1974. These references are herein incorporated in their entirety by reference.

The second step of the present method involves the detection of HCG in the concentrated sample. Preferred test methods for determining the presence of HCG in the concentrated urine or serum sample are the immunological tests referred to as agglutination and agglutination inhibition tests.

The agglutination tests, for example, see H. Fink and A. Frie, Obstet. Gynecol., 28, 660 (1966) are based on the direct reaction between HCG and a HCG-antibody.

The agglutination inhibition tests are based on an inhibition of a reaction between HCG-antiserum and HCG on a carrier, for instance, red blood cells or latex particles. When the latter test involves red blood cells it is known as the haemagglutination inhibition test and when the latter test involves latex particles it is known as the latex agglutination inhibition test. For example, see L. Wide and C. A. Gemzell, Acta Endocrinol., 35, 261 (1960); B. M. Hobson, J. Reprod. Fert., 12, 33 (1966) and references cited therein; B. M. Hibbard Brit. Med. J., 1, 593 (1971); U.S. Pat. No. 3,548,051, issued Dec. 15, 1970; U.S. Pat. No. 3,551,555 issued Dec. 29, 1970; and U.S. Pat. No. 3,666,421, issued May 30, 1972.

The HCG-antibody, required for the above tests, is known. The preparation of the antibody have been described several times, for example, see Wide and Gemzell, cited above, and A. R. Midgley, et al., Proc. Soc. Exp. Biol. Med., 108, 85 (1961). If desired HCG also can be detected by using a specific antiserum to the β-subunit of HCG, see J. Vaitukaitis, et al., J. Clin. Endocrinol., 33, 988 (1971) and Amer. J. Obstet. Gynecol., 113, 751 (1972). When the specific antiserum to the β-subunit of HCG is used, it will of course detect the presence of the β-subunit itself as well as intact HCG. (It is well known that the β-subunit of HCG readily disassociates from HCG.)

Test kits suitable for the detection of HCG in urine and serum samples according to the method of this invention are available commercially; for example, the haemagglutination inhibition test kits, for instance, Pregnosticon All-in (Organon, Holland and U.S.A.)

and UCG (Wampole Laboratories, Stamford, Conn.); latex agglutination inhibition test kits, for instance, Planotest, Pregnosticon Dri-Dot (Organon, Holland and U.S.A.), Gravindex (Ortho, Raritan, N.J., U.S.A.) and Prepurex or Prepurin (Burroughs Wellcome, U.S.A. and United Kingdom); and the direct agglutination test, for instance, DAP Test (Denver Biologicals Co. U.S.A.) and Gonavislide (Molter Gmbh., West Germany).

More specifically, in practising the method of this invention a sample of female urine or serum, the urine preferably being clarified by filtration through a suitable filter paper or by centrifugation, is concentrated 10 to 500 times, preferably 10 to 50 times by placing the sample in contact with an ultrafiltration membrane having a molecular weight cut-off ranging from about 10,000 to about 50,000, preferably about 15,000 to 35,000. In other words, a lower limit of 10,000 or preferably 15,000 and an upper limit of 50,000, preferably an upper limit of 35,000, have been found useful. The sample is filtered through the membrane until the unfiltered portion of the sample (retentate) has reached the desired degree of concentration. The concentration step is carried out usually at temperatures ranging from about 0° to 40° C, preferably 4° to 25° C and usually takes 1 to 2 hours. The filtrate is discarded and the retentate is subjected to an immunological test for HCG according to one of the methods mentioned above. concentrated -HCG-antiserum, bottom of The aqueous solution of the concentrated urine or serum is mixed in an ampoule with the regularly recommended amount of a lyophilized mixture of HCG- or β-antiserum, erythrocytes or latex particles sensitized with HCG, buffer, preservative and excipients. After allowing the mixture to stand for about 1 to 2 hours, a positive reaction is indicated by a specific sedimentation pattern in the form of a clearly defined ring at the bottm fo the ampoule if the ampoule is round bottomed or in the form of a dot if the ampoule has a conical-shaped bottom; a negative reaction is indicated by a diffuse yellow-brown sediment.

Alternatively, latex agglutination or direct agglutination tests, see above, are used for the detection of HCG in the aqueous solution of concentrated urine.

In a preferred modification of the above noted practice of this invention, it has been found advantageous to subject the inner surface of the concentrator, i.e., the chamber containing the ultrafiltration membrane, to a prewash with a 0.1 to 5%, preferably 0.1 to 1.0% aqueous solution of bovine serum albumin (BSA) solution to contact the inner surfaces of the concentrator for about one minute prior to placing the sample of urine in the concentrator. This modification results in more clearly defined positive and negative reactions and improves the sensitivity of the present method by blocking absorption of HCG on the surface of the device.

Furthermore, it has been found that the same advantageous results are obtained if the BSA is used to wash the aforementioned filter paper used to filter the urine or serum sample or if BSA is added directly to the initially collected urine sample to give a concentration ranging from 0.001 to 1.0%, preferably 0.01 to 1.0% BSA in the urine.

Proteins other than BSA also are suitable for the afore-mentioned purpose; e.g., human serum albumin, egg albumin, gamma globulin (both bovine and human), myoglobin, fibrinogen, human hemoglobin, gelatin and keyhole limpet hemocyanin.

Although it may appear obvious to concentrate a dilute solution of HCG so that the concentration of HCG falls within the sensitivity range of a given test, it is in direct contradiction to the cumulative experience with immunological tests for the determination of HCG in body fluids. In the first place it will be appreciated that concentration of such body fluids as urine and serum likewise concentrates those substances which interfere with the immunological test. Secondly, there is good authority that concentration of body fluids such as urine increases the occurrence of false positives; see, for example, L. Wide, Acta Endocrinol., Suppl, 70 (1962) pp. 95 and 100, and M. Hobson, cited above, p. 43.

More explicitly, Wide recommends strongly that immunological tests be adjusted so that a positive test be obtained only when the concentration of HCG in urine is 1000 or more m.i.u./ml. Otherwise, the levels of LH or human menopausal gonadotropin, occurring in some samples, may interfere with the specificity of the HCG assay leading to false positives.

One attempt to overcome the situation is described by R. T. Fisk in U.S. Pat. No. 3,171,783, issued Mar. 2, 1965. According to the method of the Fisk Patent, which is much more complicated than the ultrafiltration method of the present invention, HCG in the urine is concentrated by absorption on kaolin. However, after absorption of the HCG according to this procedure at least three more steps must be carried out before proceeding with an immunological test for HCG. A similar elaborate technique based also on absorption of kaolin was described earlier by E. H. Hon and J. McL. Morris, Yale J. Biol. Med., 27, 178 (1954). Further evidence for the complexity of these two methods are that they have never been used widely by practitioners, see Hobson, cited above, and Hibbard, cited above. Furthermore, these latter methods and another related method of the prior art, B. M. Hobson and L. Wide, Acta Endocrinol., 46, 632 (1964), result in about a 50% loss of activity of the gonadotropin with a consequential loss of sensitivity; also the chance of obtaining false positives results in some instances, e.g. urine samples from premenopausal, menopausal or post-menopausal women is increased.

The device of this present invention is shown in several embodiments in FIGS. 1 – 14 of the accompanying drawings wherein:

FIG. 1 represents a perspective view of the inner and outer components of one emobodiment of the device in separated spaced relationship prior to insertion of the former into the latter;

FIG. 2 represents a vertical cross-sectional view of the inner and outer components of FIG. 1 in fixed operational relationship prior to urine concentration;

FIG. 3 represents a vertical cross-sectional view of the inner and outer components of FIG. 1 in operational relationship subsequent to urine concentration with the inner component partially withdrawn;

FIG. 4 represents a horizontal corss-sectional view along line 4—4 of FIG. 2;

FIG. 6A heads up a sheet of the accompanying drawings;

FIG. 7 is found on the sheet of accompanying drawings beginning with FIG. 5;

FIG. 9 is found on the sheet of accompanying drawings beginning with FIG. 5;

FIG. 10 represents a vertical cross-sectional view of a further embodiment of the device of this invention;

FIG. 11 represents a horizontal cross-sectional view taken along line 11—11 of FIG. 10;

FIG. 12 represents a perspective view of the membrane, including the impermeable lower section thereof, of the embodiment of FIG. 10;

Figure 5:
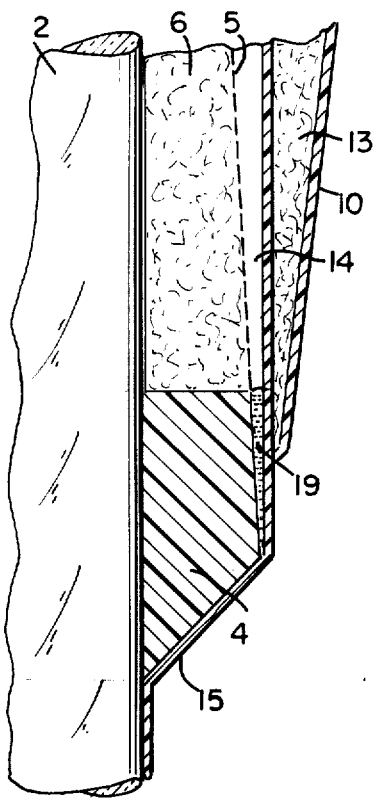
FIG. 5 represents an enlarged partial section of FIG. 2 additionally showing the urine concentrate.

In one exemplified embodiment of the method of this invention, concentration of a urine sample is effected by the use of a Minicon-B-15 ultrafiltration concentrator supplied by Amicon Corporation, Lexington, Mass., U.S.A. According to the manufacturer the Minicon-B-15 concentrator is based on the principle of backing an anisotropic Diaflo ultrafiltration membrane having a molecular cut-off of 15,000, with absorbent pads. In another run, the Minocon-PM-30, by the same manufacturer was used; this concentrator is made on the same principle as the Minicon-β-15 and has a molecular cut-off of 30,000. Concentrators of this particular design are described in U.S. Pat. No. 3,817,379, cited above.

With reference to the present embodiment, a 5 ml. sample of first voided morning urine, filtered through Whatman No. 1 filter paper, was concentrated by placing the sample in a well of the Minicon-B-15 concentrator. During the concentration step the concentrator was allowed to stand in an ambient temperature of about 4° C. After a period of about two hours the sample had concentrated to about 0.1 ml. The concentrated urine (retentate) was removed from the concentrator and diluted back to a volume of 0.5 ml with distilled water to give the aqueous solution of the concentrated urine. Removal of the retentate was done by using a fine Pasteur pipette. Thereafter, the aqueous solution of concentrated urine was tested for the presence of HCG by a test kit for determining HCG in urine. The test kit was a haemagglutination inhibiton test kit, called the Pregnosticon All-in.

Turning now to FIG. 1, inner component 1 is comprised of rod 2, spaced apart collars 3 and 4 connected by ultrafiltration membrane 5 surrounding absorbent 6. Rod 2 is equipped with handle 7 for ease of insertion and withdrawal and an end portion projecting beyond collar 4 to act as a plug. Collar 3 and 4 surround rod 2, collar 4 being fluid impermeably sealed to rod 2 and collar 3 being so fitted as to allow for escape of air from absorbent 6.

Outer component 8 is comprised of inner and outer walls 9 and 10, respectively, joined by member 11 to provide a funnel shaped top opening 12. Inner and outer walls 9 and 10 enclose absorbent 13.

Referring to FIG. 2, outer component 8 is adapted to receive inner component 1 to provide annular space 14 and is adapted in its lower portion by wall 15 to receive collar 4 and the lower end portion of rod 2 in fluid impermeable sealed relationship. Outer component 8 includes integrally therewith an appending reagent receptacle 17 containing reagent 17a. Also inner wall 9 of outer component 8 has an opening 18 through wall 9 leading to absorbent 13.

In utilizing the embodiments of the invention shown in FIGS. 1 through 5 to test for pregnancy, a urine sample of a woman is filtered, for example, through Whatman No. 1 filter paper or centrifuged, for example, at 3000 rpm for 5 minutes, and poured into funnel shaped top opening 12 of the unit as shown in FIG. 2. The urine flows down and fills annular space 14 and any excess over, for example, 5 ml, flows through opening 18 and is absorbed by absorbent 13. The ultrafiltration membrane 5 is selected to provide a molecular weight cut-off of about 10,000 to 50,000, preferably 15,000 to 35,000, so as not to permit passage of human chorionic gonadotropin. Such membranes are described above.

A portion of the urine in annular space 14 passes through ultrafiltration membrane 5 and is absorbed by absorbent 6, the displaced air escaping upwardly past collar 3. When the level of concentrate in annular space 14 reaches the upper surface of collar 4, i.e. impermeable dead stop zone, after about 2 hours, no further concentration can take place as shown at 19 in FIG. 5 and the concentrate comprises a predetermined amount, for example 0.5 ml. Inner component 1 is lifted from outer component 8 permitting passage of the concentrate around the end portion of rod 2 projecting beyond collar 4 (i.e., the plug portion of rod 2) and into receptacle 17.

Positioned in receptacle 17 is reagent 17a which is a lyophilized mixture of HCG or β-HCG antiserum, erythrocytes or latex particles sensitized with HCG, buffer, preservative and excipients.

Figure 6:
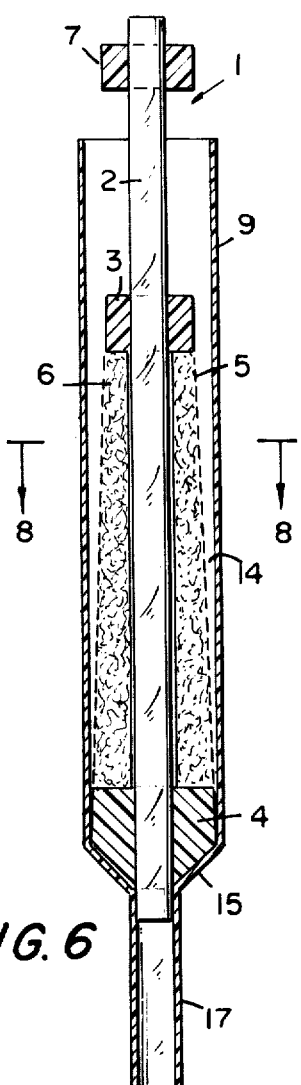
FIG. 6 represents a vertical cross-sectional view similar to FIG. 2 of another embodiment of the device of this invention for use with a pre-selected urine volume.

After one and a half to two hours, a reading is made and if the woman is pregnant, a specific sedimentation pattern in the form of a clearly defined ring or dot appears depending on the shape of the bottom of the receptacle 17, i.e., round-bottomed or wedged shape. If no ring or dot appears, the female is not pregnant. For reading the test results, the rod 2 can be made of glass or a clear plastic material such that the ring or dot can be viewed by the operator by sighting down the rod. In this circumstance, the lower portion of chamber 17 is made of a translucent material. A mirror 20 disposed under chamber 17 as shown in FIG. 6 simplifies reading the test results.

FIGS. 6, 6A, 6B, 6C and 8 show an alternative embodiment wherein the device is not equipped for overflow and requires premeasurement of the urine sample. Thus inner component 1 is the same and the outer component does not include outer wall 10 and absorbent 13.

Figure 7:
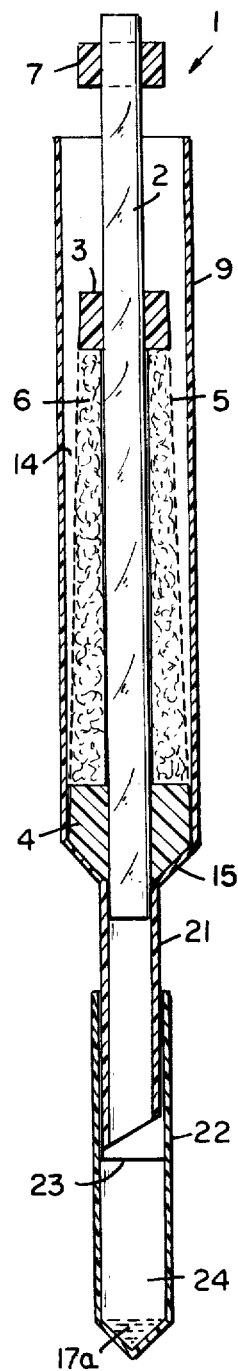
FIG. 7 represents a vertical cross-sectional view of an embodiment similar to that shown in FIG. 6 but including a separable reagent chamber.
Figure 9:
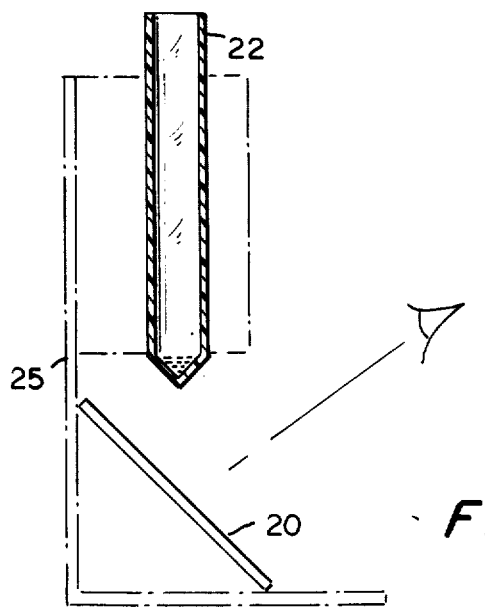
FIG. 9 represents a cross-sectional view of the separated reagent chamber of FIG. 7 mounted for analysis.
Figure 6A:
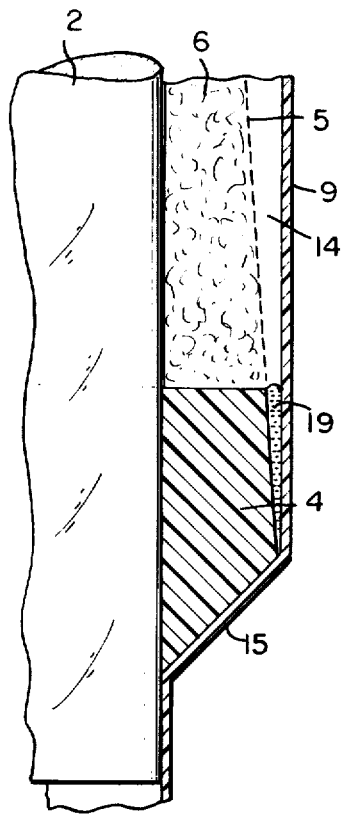
FIG. 6A represents an enlarged partial section of FIG. 6 similar to FIG. 5.
Figure 6B:
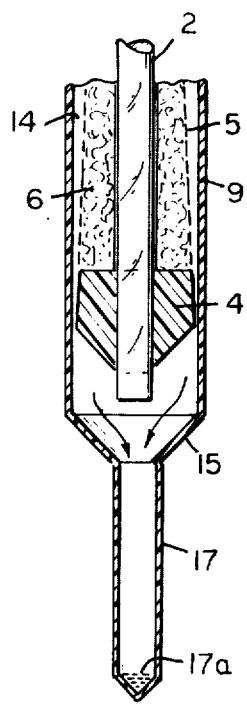
FIG. 6B represents a partial vertical cross-sectional view similar to FIG. 3 of the embodiment of FIG. 6.
Figure 7A:
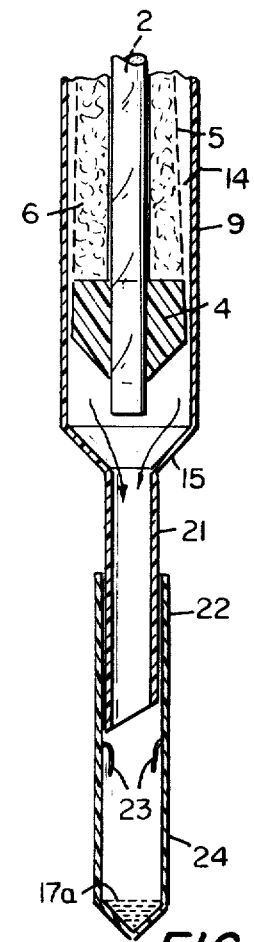
FIG. 7A represents a vertical cross-sectional view of the embodiment of FIG. 7 with the inner component partially withdrawn.
Figure 6C:
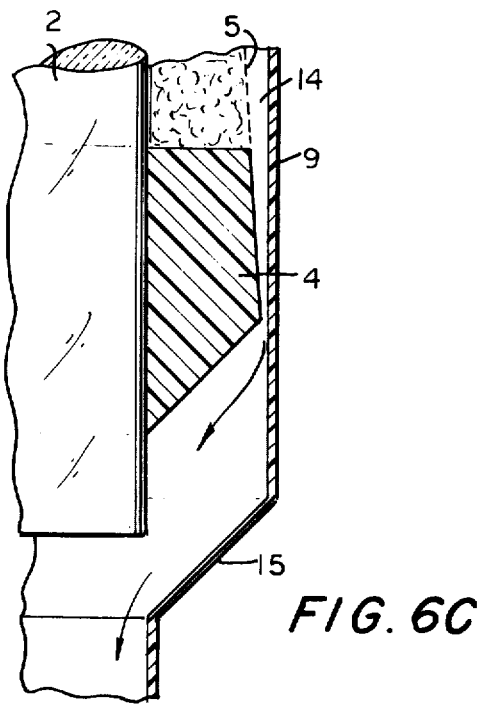
FIG. 6C represents and enlarged partial section of FIG. 6B.
Figure 8:
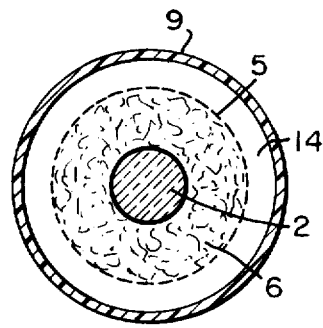
FIG. 8 is a horizontal cross-sectional view taken along line 8—8 of FIG. 6.

FIG. 7, 7A and 9 show an alternative embodiment wherein component 1 is the same and the outer component is constructed in two pieces. Thus in FIG. 7, the outer component is comprised of wall 9, lower portion wall 15 and spout 21. Below and slideably surrounding spout 21 is receptacle 22 having closure membrane 23 defining a closed section 24 containing reagent 17a.

In FIG. 7A, membrane 23 is shown ruptured after further insertion into receptacle 22 of spout 21, and inner component 1 in partially withdrawn or raised position.

FIG. 9 shows the receptacle 22 separated from spout 21 of FIG. 7 mounted on support rack 25 also containing mirror 20.

In the embodiment of FIGS. 10 and 11 the chamber 26 is in the form of a right square prism and is defined by impermeable walls 27, 28, 29 and 30 and within chamber 26 is positioned pyramidally shaped, ultrafiltration membrane 31, surrounded on its outside periphery by absorbent 32. Within the space 32a defined by pyramidally shaped membrane 31 (including the fluid impermeable pyramidally shaped lower section 32b, i.e. the impermeable "dead stop zone") is positioned ampoule 33 containing reagent 34 maintained under vacuum. In the lower section 32b is a depression 35 adapted to receive snugly the stem 36 of ampoule 33. In this embodiment the stem 36 is prestressed at the point 32c which corresponds to the bottom of impermeable lower section 32b.

The pyramidally shaped form of member 31 including its lower section 32b for the embodiment of FIGS. 10 and 11 is shown in FIG. 12.

In operation of the embodiment of FIG. 10, urine is introduced into space 32a surrounding ampoule 33 and is concentrated to a retentate. The ampoule 33, fitted snugly in depression 35, is then broken at the prestressed point. The retentate is necessarily drawn into previously evacuated ampoule 33 and contacts reagent 34; the ampoule 33 is inverted, contents mixed thoroughly, and then placed in a rack to be viewed.

Figure 13:
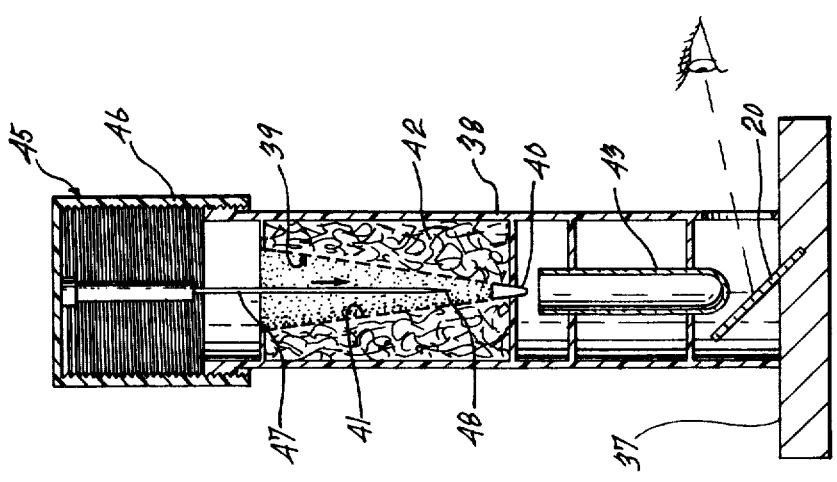
FIG. 13 represents a vertical cross-sectional view of still a further embodiment of the device of this invention.

In still another embodiment of the device of this invention, reference is made to FIG. 13. In FIG. 13, a base 37 is shown supporting outer wall 38. Outer wall 38 supports a cone shaped member 39, the lower portion 40 of said member 39 is formed of a fluid impermeable material and the upper portion 41 of said member 39 is formed of an ultrafiltration membrane. Positioned adjacent to membrane 41 is absorbent 42 in effective contact with the outside surface of the membrane 41. Disposed beneath the impermeable portion 40 of cone shaped member 39 is reagent receptacle 43 and disposed beneath receptacle chamber 43 is mirror 20. The portion of outer wall 38 surrounding the receptacle and the receptacle itself are made of a material transparent to light. Positioned above outer wall 38 is cap 45 having depending therefrom circumferential wall 46 and plunger 47 with a pointed tip 48.

In operation, urine is measured into cap 45, the urine is poured into cone shaped member 39, the fluid passes through upper portion 41 and into absorbent 42 and the retentate is collected within impermeable lower portion 40. When the retentate has collected, cap 45 is forced down, as by being threadedly engaged, such that the point 48 of plunger 47 ruptures impermeable wall 40 of member 39. When the plunger 47 is withdrawn, the retentate flows through the rupture and into reagent receptacle 43. The reaction can be read by removing the reagent receptacle or by means of a mirror 20 placed beneath reagent receptacle 43.

Figure 14:
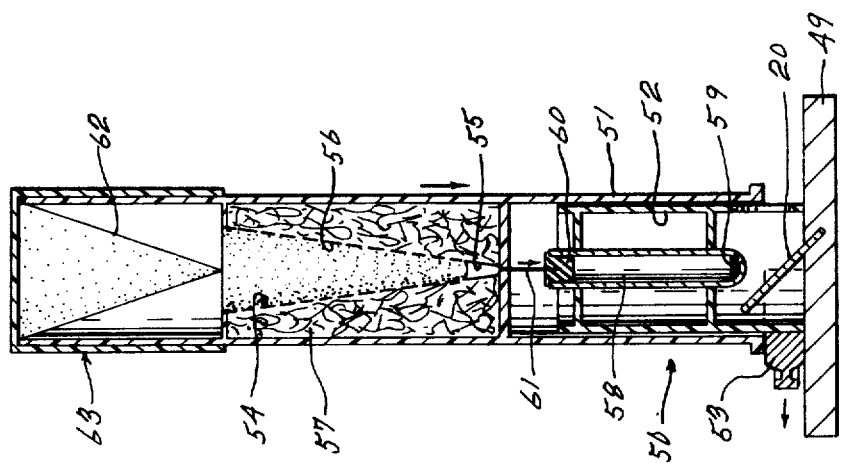
FIG. 14 represents a vertical cross-sectional view of still another embodiment of the device of this invention.

Still another embodiment is illustrated by FIG. 14. This embodiment comprises a base 49 supporting telescopic member 50. Telescopic member 50 consists of a outer wall member 51 and an inner wall member 52; the latter being slideably received in the former. Removable abutment member 53 is placed between the outer wall member 51 and the base 49 to position the outer and inner wall members 51 and 52 with respect to each other. Outer wall member 51 supports pyramidally shaped member 54; the lower portion 55 of said member 54 being in the form of a fluid impermeable material and the upper portion 56 of said member 54 being an utltrafiltration membrane. Positioned adjacent to member 54 is absorbent 57 in effective contact with the outer surface of the upper portion of membrane 56. Disposed below impermeable portion 55 and supported by brackets positioned on the lower wall member 52 is reagent receptacle 58 containing the reagent 59 maintained under vacuum by rubber seal 60. A hollow tube 61 depends from the bottom of the lower impermeable portion 55 and said tube is in fluid-flow communication with said lower portion 55, seal 60 sealing the bottom of the tube 61. Positioned over the upper portion 54 and supported by outer wall member 51 is filter 62. The device of this embodiment is provided further with removable dust cap 63, and mirror 20 disposed below the reagent receptacle 58.

In operation, a predetermined quantity of urine is filtered through the filter 62 and is collected in pyramidally shaped member 54. Sorbable fluid passes through the upper portion 56 into absorbent 57 and the retentate collects in fluid impermeable lower portion 55. When the retentate has collected, abutment member 53 is removed and upper wall is pushed down toward base 49 so that the lower tip of the hollow rod 61 ruptures the seal 60 and the retentate flows by vacuum assistance into the reagent receptacle 58. The device is separated by withdrawing outer wall member 51 up and away from the inner wall member 52 leaving a lower portion of the device comprising base 49, inner wall member 52, mirror 20 and reagent receptacle 58. After the reaction between the retentate and reagent has occurred, the results of the reaction are read by means of mirror 20 positioned below the receptacle 58.

Figure 15:
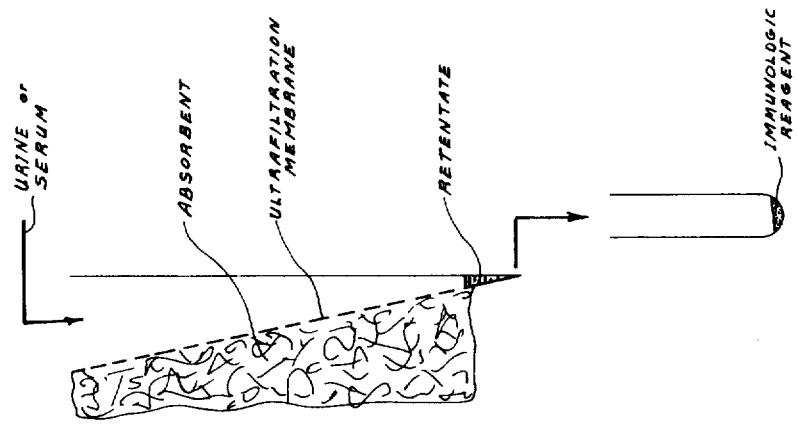
FIG. 15 is a schematic representation of the invention.

FIG. 15 represents schematically the steps of concentrating gonadotropin-containing urine or serum with the ultrafiltration membrane, said membrane being in effective contact with an absorbent capable of sorbing biological fluid to obtain a retentate, and reacting the retentate with a reagent capable of detecting the presence of the gonadotropin.

With reference to the materials useful for the manufacture of the device of this invention a description of the ultrafiltration membrane and the absorbent is found in the above noted references on ultrafiltration membranes, for example, see U.S. Pat. No. 3,817,379, noted above.

Regarding the portions of the apparatus other than the ultrafiltration member, the apparatus may be made from any suitable impermeable material which can be molded easily into the desired shape. Glass or plastic can be used. A thermoplastic material or catalytically cured plastic for instance, polyethylene, polypropylene or polystyrene, is most economical and adequate for this purpose.

The sensitivity of the method of this invention for detecting HCG in urine is demonstrated by an experiment in which predetermined amounts of HCG are added to normal urine (i.e., HCG-free urine), which is then assayed by the present method. Following Table I illustrates the results of such experiments wherein a predetermined amount of HCG (APL of Ayerst Laboratories, New York, U.S.A.) is dissolved in urine collected from a woman on the 16th and 17th day of a regular cycle and from a postmenopausal woman to give urine samples containing 20, 40 and 80 m.i.u/ml of HCG. (It should be noted that currently practiced pregnancy tests can give "false positive" results from urine samples of such women.) Thereafter, the samples are subjected to the concentration and detection steps of the exemplified embodiment, described herein, using a 1% BSA prewash for the concentrator. The urine sample serves as its own control and all assays are done in duplicate.

was subsequently clinically confirmed by a physician. Each daily sample was assayed by first a recognized haemagglutination inhibition test (HIT), secondly by the haemagglutination inhibition test preceded by first concentrating the urine sample by an acetone precipitation method (AE-HIT), and, thirdly, by concentrating the sample by ultrafiltration followed by detection of the HCG by a haemagglutination inhibition test (UF-HIT). In the latter assay (UF-HIT) the procedure used was that described herein as the exemplified embodiment method using a 1% BSA prewash for the concentrator.

For the HIT, a Pregnosticon All-in test kit was employed. A first voided morning urine sample (0.1 ml), previously filtered through Whatman No. 1 filter paper, is diluted with 0.4 ml of distilled water and the resultant mixture is subjected to the immunological test reaction for about 2 hours.

For the AE-HIT, a known acetone precipitation

TABLE I

| URINE SAMPLE NO. | DAY AFTER THE FIRST DATE OF THE LAST MENSES OR POSTMENO-PAUSAL (PM) | GROUPS (HCG, m.i.u./ml. of URINE) | RESULTS OBTAINED ACCORDING TO PRESENT METHOD, STRONG POSITIVE (++), POSITIVE (+), UNCERTAIN (±), NEGATIVE (−) |
|---|---|---|---|
| 1 | 16 | Control | − |
| 1 | 16 | Plus HCG (20) | ± |
| 1 | 16 | Plus HCG (40) | + |
| 1 | 16 | Plus HCG (80) | ++ |
| 2 | 17 | Control | − |
| 2 | 17 | Plus HCG (20) | ± |
| 2 | 17 | Plus HCG (40) | + |
| 2 | 17 | Plus HCG (80) | ++ |
| 3 | PM | Control | − |
| 3 | PM | Plus HCG (40) | + |
| 3 | PM | Plus HCG (80) | ++ |
| 4 | PM | Control | − |
| 4 | PM | Plus HCG (40) | + |
| 4 | PM | Plus HCG (80) | ++ |

The results of the aforementioned experiment show that the method of this invention consistently detects HCG in urine at concentrations of 40 m.i.u./ml or more. These results indicate that the present method has a far greater sensitivity for detecting HCG in urine than other presently available in vitro tests with the exception of the elaborate RIA and radioreceptor methods mentioned earlier. The results are even more significant when it is realized that concentrations of HCG of less than 500 m.i.u./ml of urine are not detected with presently widely used pregnancy test kits, see S. G. Driscoll, et al., Am. J. Obstet. Gynecol., 110, 1083 (1971), D. A. Edelman, et al., Am. J. Obstet. Gynecol., 119, 521 (1974), H. Hepp and R. H. Richter, Med. Klin., 68, 920 (1973) and M. L. Taymor, Medical World News, Feb. 1, p. 24 (1974). See also Medical Letter, 17, 6 (1975). As noted above, an adjustment of the commercial kits to detect lower concentrations of HCG results in an increased occurrence of "false positives." Since concentrations of HCG in pregnancy urine of about 40 m.i.u./ml are obtained during the first week of pregnancy; for example, see L. Wide, Lancet, 2, 863 (1969), this present method provides a good test for giving a definite indication of pregnancy as early as the first week thereof.

The improved reliability of the method of this invention over currently used in vitro methods for detecting pregnancy, especially early pregnancy, is demonstrated in a comparative study wherein consecutive daily samples of urine are assayed. For example, the following Table II illustrates the results of such an experiment wherein consecutive daily samples of urine were collected and assayed from subjects in which pregnancy method, for example, see L. Wide and C. Gemzell, Acta Endocrinol., 39, 539 (1962), is employed. More explicitly, 50 ml of filtered (Whatman No. 1 filter paper), first morning urine (pH 5.0 by adding 1% acetic acid) was added to 100 ml of cold acetone. The mixture was kept at 4° to 10° C for 1 hour and then centrifuged at 4,000 rpm at 20° - 25° C for 10 minutes. The supernatant layer was discarded and the precipitate dried under a stream of air for 10 minutes and then in a vacuum desiccator for ten minutes. The dried precipitate was dissolved in 1.25 ml of distilled water. The solution was centrifuged as before for 5 minutes and an aliquot of 0.5 ml (equivalent to 20 ml original urine) of supernatant solution was used for the subsequent HIT.

TABLE II

| PREGNANT SUBJECT NO." | URINE SAMPLES TESTED BEFORE (−) OR AFTER (+) THE EXPECTED DATE OF MENSES (0) | RESULTS POSITIVE (+) NEGATIVE (−) UNCERTAIN (±) | | |
|---|---|---|---|---|
| | | HIT | AE-HIT | UF-HIT |
| 65 | +1 | − | ± | + |
| | +2 | − | + | + |
| | +3 | − | ± | + |
| | +4 | − | − | + |
| | +5 | − | − | + |
| | +6 | ± | ± | + |
| 66 | 0 | − | − | + |
| | +1 | − | + | + |
| | +2 | − | ± | + |
| | +3 | − | ± | + |
| | +4 | − | ± | + |

TABLE II-continued

| PREGNANT SUBJECT NO.* | URINE SAMPLES TESTED BEFORE (−) OR AFTER (+) THE EXPECTED DATE OF MENSES (0) | RESULTS POSITIVE (+) NEGATIVE (−) UNCERTAIN (±) | | |
|---|---|---|---|---|
| | | HIT | AE-HIT | UF-HIT |
| | +5 | + | + | + |
| | +6 | + | − | + |
| 98 | −3 | − | ↑ | − |
| | −2 | − | | + |
| | −1 | − | | + |
| | 0 | − | Not done | + |
| | +1 | − | | + |
| | +2 | − | | + |
| | +3 | − | | + |
| | +4 to +8 | Not done | | Not done |
| | +9 | + | ↓ | + |
| 105 | − | − | ↑ | − |
| | −2 | − | | + |
| | −1 | − | | + |
| | 0 | − | | + |
| | −1 | − | | + |
| | 2 | − | Not done | + |
| | 3 | − | | + |
| | 4 | − | | + |
| | 5 | Not done | | Not done |
| | 6 | − | | + |
| | 7 | − | ↓ | + |
| | 8 | + | | + |

*pregnancy subsequently confirmed clinically in all cases

From the preceding comparative study it is concluded that the method of this invention is more simple and reliable for detecting pregnancy than the standard methods mentioned above. Furthermore, it is capable of detecting pregnancy earlier than these standard methods; namely, it is a more sensitive method.

In another group of four patients pregnancy was detected by the method of this invention between the second and fifth day after the expected and missed menstrual period whereas pregnancy could not be detected during this period in these subjects according to the above HIT procedure. Subsequently, pregnancy was clinically confirmed in all the four cases.

Significant results were obtained also in cases where a woman went beyond her expected date of menses but subsequently menstruated. In these cases a negative test proved to be 100% correct as demonstrated by the subsequent menstruation. In many instances a negative result obtained according to the method of this invention relieved anxiety during the delayed menstruation period. The results of these latter tests are illustrated by the following Table III involving women who were latter shown clinically to be non-pregnant.

TABLE III

| Subject No. | Urine samples tested days before (−) or after (+) the expected date of menses (O) | UF-HIT |
|---|---|---|
| 53 | −3 | − |
| | −2 | − |
| | −1 | − |
| | First 0 | − |
| | cycle +1 | − |
| | +2 | − |
| | +3 | − |
| | +4 | − |
| | +5 | − |
| | −5 | − |
| | −4 | − |
| | Second −3 | − |
| | cycle −2 | − |
| | 0 | − |

TABLE III-continued

| Subject No. | Urine samples tested days before (−) or after (+) the expected date of menses (O) | UF-HIT |
|---|---|---|
| | +1 | − |
| | +8 | − |
| 55 | −1 | − |
| 56 | +3 | − |
| 57 | +30 | − |
| 58 | +14 | − |
| 59 | 0 | − |
| 60 | +18 | − |
| 61 | +2 | − |
| | +7 | − |
| 62 | +9 | − |
| 65 | +4 | − |
| 66 | −1 | − |
| 67 | −2 | − |
| 69 | −6 | − |
| | −5 | − |
| | −4 | − |
| | −3 | − |
| | 0 | − |
| 77 | +5 | − |
| | +12 | − |
| 83 | +8 | − |
| 100 | +2 | − |
| | +5 | − |
| 106 | +4 | − |
| | +8 | − |
| 109 | +2 | − |
| 110 | −3 | − |
| | −2 | − |
| | 0 | − |
| | +1 | − |
| | +2 | − |
| | +3 | − |
| 112 | −4 | − |
| | −3 | − |
| | 0 | − |
| | +1 | − |
| | +2 | − |
| | +3 | − |
| 119 | +4 | − |

It has been found that in the method of the present invention the occurrence of false positives is substantially reduced. The latter aspect is demonstrated further by the obtention of consistent negative tests when the method of this invention is applied to urine from groups of ovulating (Table III) and postmenopausal women; it being well known that urine samples from the above two groups may give rise to the occurrence of false positives when assayed by presently used pregnancy tests.

Although the foregoing data uses the human female as the subject, this invention may find applicable for determining pregnancy in all mammals secreting a gonadotropin of pregnancy; for example, the equine species.

The success of the method of this invention, its capability of detecting very minute quantities of HCG with a very high degree of accuracy, the significant reduction of false negatives, and the reduction of "false positives" are predicated upon the selection of a suitable ultrafiltration membrane. The membrane allows the passage of inert materials and of substances interfering with the subsequent immunological test into the filtrate, while retaining the HCG present in the sample of body fluid. In this manner we have succeeded in establishing the presence of pregnancy as early as the 26th day of a regular 28-day menstrual cycle without having to resort to RIA or the radioreceptor method. In some cases this means that pregnancy is being detected 10 to 12 days after conception whereas most pregnancy tests available today do not detect pregnancy until about 24 to 26 days after conception.

An alternative embodiment of the present invention is the employment of the above method for the assessment of pituitary and gonadal function, for instance, ovulation, by using LH-antibiodies and LH-antigen in the immunological reagent instead of the HCG-antibody and antigen.

Still other alternative embodiments include the employment of the method for determining estrogen deficiency states in humans using antibodies to the human gonadotropins, follicle-stimulating hormone (FSH) and human menopausal gonadotropin (HMG).

Appropriate antibodies, i.e., anti-LH, N. R. Moudgal and H. G. Madwa Raj, Pituitary Gonadotrophins in "Methods of Hormone Radioimmunoassay," B. M. Jaffe and H. R. Behrman, Ed., Academic Press, New York, 1974, page 75; anti-FSH, A. H. W. M. Schuurs and C. J. Van Wijngaarden, J. Clin. Endocrinol. Metabol., 40, 619 (1975); and anti-HMG, B. Lunenfeld, et al., J. Clin. Endocrinol. Metabol., 21, 478 (1961), and antigens (LH, FSH or HMG) would replace HCG antibody and antigen as elements for these alternative embodiments.

We claim:
1. A pregnancy test device suitable for the detection of human chorionic gonadotropin or its β-subunit thereof in urine or serum, which comprises:
   a. chamber means including a ultrafiltration membrane for concentration of the urine or serum and means for collecting the concentrate;
   b. means for transferring the collected concentrate to a detection receptacle means;
   c. detection receptacle means for the detection of human chorionic gonadotropin or its β-subunit thereof in the concentrate by immunological means; and
   d. wherein said chamber means including an ultrafiltration membrane has been prewashed with a solution of protein.

2. A pregnancy test device suitable for the detection of human chorionic gonadotrophin or its β-subunit thereof in serum or urine, which comprises:
   a. a chamber, open at the top and closed at the bottom, having the upper portion of at least one wall formed of an ultrafiltration membrane permeable to urine or serum and capable of selective retention of human chorionic gonadotropin, and all other walls formed of a rigid impermeable material;
   b. a layer of absorbent capable of sorbing urine or serum passing through said membrane, said absorbent being contiguous to the outside surface of said membrane and in effective contact with said membrane;
   c. said chamber including a lower portion, all walls of which are impermeable, for retaining a fixed volume of urine or serum concentrate containing human chorionic gonadotropin;
   d. outlet means in the lower portion of said chamber and means for opening said outlet means; and
   e. a reagent receptacle connected to said chamber through said outlet means, said reagent receptacle adapted to receive a reagent for the immunological determination of human chorionic gonadotropin or the β-subunit thereof and means for viewing the reaction of the reagent therein with said urine or serum concentrate containing human chorionic gonadotropin.

3. The device of claim 2 including a filter disposed for filtering urine being introduced into the chamber.

4. A pregnancy test device suitable for the detection of human chorionic gonadotrophin or its β-subunit thereof in serum or urine, which comprises:
   a. a chamber, open at the top and closed at the bottom, having the upper portion of at least one wall formed of an ultrafiltration membrane permeable to urine or serum and capable of selective retention of human chorionic gonadotropin, and all other walls formed of a rigid impermeable material;
   b. a layer of absorbent capable of sorbing urine or serum passing through said membrane, said absorbent being contiguous to the outside surface of said membrane and in effective contact with said membrane;
   c. a filter disposed above the chamber for filtering urine or serum being introduced into the chamber;
   d. said chamber including a lower portion, all walls of which are impermeable, for retaining a fixed volume of urine or serum concentrate containing human chorionic gonadotropin;
   e. outlet means in the lower portion of said chamber;
   f. tubular means adapted to penetrate said outlet means to said concentrate collected in the lower portion of said chamber; and
   g. a reagent receptacle removably connected to said chamber, said reagent receptacle adapted to receive a reagent for the immunological determination of human chorionic gonadotropin or the β-subunit thereof and means for viewing the reaction of the reagent therein with said concentrate containing human chorionic gonadotropin.

5. The pregnancy test device of claim 2 wherein said chamber containing said ultrafiltration membrane has been prewashed with a solution of protein.

6. The device of claim 3 wherein said filter has been prewashed with a solution of protein.

7. The device of claim 3 wherein said chamber containing said ultrafiltration membrane, and said filter have been prewashed with a solution of protein.

8. The pregnancy test device of claim 4 wherein said chamber containing said ultrafiltration membrane has been prewashed with a solution of protein.

9. The device of claim 4 wherein said filter has been prewashed with a solution of protein.

10. The device of claim 4 wherein said chamber containing said ultrafiltration membrane, and said filter have been prewashed with a solution of protein.

* * * * *